(12) United States Patent
Silvestri et al.

(10) Patent No.: US 11,994,418 B2
(45) Date of Patent: May 28, 2024

(54) OPTICALLY POWERED SENSING SYSTEM AND METHOD FOR HAZARDOUS ENVIRONMENTS

(71) Applicant: NewSouth Innovations Pty Limited, Sydney (AU)

(72) Inventors: Leonardo Silvestri, Sydney (AU); Francois Ladouceur, Sydney (AU); Zourab Brodzeli, Sydney (AU)

(73) Assignee: NewSouth Innovations Pty Limited, Sydney (AU)

( * ) Notice: Subject to any disclaimer, the term of this patent is extended or adjusted under 35 U.S.C. 154(b) by 0 days.

(21) Appl. No.: 17/907,065

(22) PCT Filed: Mar. 24, 2021

(86) PCT No.: PCT/AU2021/050263
§ 371 (c)(1),
(2) Date: Sep. 22, 2022

(87) PCT Pub. No.: WO2021/189106
PCT Pub. Date: Sep. 30, 2021

(65) Prior Publication Data
US 2023/0120640 A1   Apr. 20, 2023

(30) Foreign Application Priority Data
Mar. 24, 2020   (AU) .............................. 2020900899

(51) Int. Cl.
*G01D 5/353* (2006.01)
*H04B 10/80* (2013.01)

(52) U.S. Cl.
CPC ....... *G01D 5/35341* (2013.01); *H04B 10/807* (2013.01); *G01D 5/35383* (2013.01)

(58) Field of Classification Search
CPC .......... G01D 5/35341; G01D 5/35383; G01D 5/268; H04B 10/807; H04Q 2209/30;
(Continued)

(56) References Cited

U.S. PATENT DOCUMENTS 5,223,707 A  *  6/1993  Bjork .................... G01D 5/268
                                                             398/171
5,528,409 A       6/1996  Cucci et al.
(Continued)

FOREIGN PATENT DOCUMENTS

KR     20190115732 A    10/2019
WO       2013110141 A1   8/2013

OTHER PUBLICATIONS

"International Search Report and Written Opinion of the International Searching Authority", International Application No. PCT/AU2021/050263, dated May 25, 2021, 9 pp.
(Continued)

*Primary Examiner* — Thanh Luu
*Assistant Examiner* — Monica T Taba
(74) *Attorney, Agent, or Firm* — Myers Bigel, P.A.

(57) ABSTRACT

A sensing system including: a sensor located in an external environment, including: an electrically powered sensor element sensing an environment variable and converting the sensing to a corresponding analog electrical value measure; an electrically powered sensor value conversion system connected to the electrically powered sensor and converting the analog electrical value measure to a digital measure, in addition to encoding the digital measure with sensor identification information; a transducer element for sending the sensed data information over an optical conduit for inputting an optical power signal and outputting optical sensed data information; a coupler splitting a first portion of the optical power signal to an energy storage system; and an energy
(Continued)

storage system converting the first portion of the optical power signal into corresponding electrical energy and storing it for on demand usage; said electrically powered sensor value conversion system being supplied with electrical power from said energy storage system.

11 Claims, 5 Drawing Sheets

(58) Field of Classification Search
CPC ....... H04Q 2209/826; H04Q 2209/883; H04Q 2209/886; H04Q 9/00; H04Q 2209/82; G08C 23/06; H02H 9/008
See application file for complete search history.

(56) References Cited

U.S. PATENT DOCUMENTS

| | | | | |
|---|---|---|---|---|
| 5,814,830 A | * | 9/1998 | Crowne | G01F 23/80 340/623 |
| 5,862,287 A | * | 1/1999 | Stock | H01S 3/0057 359/332 |
| 6,850,539 B1 | * | 2/2005 | Cassiers | H04W 52/04 370/465 |
| 2005/0184260 A1 | | 8/2005 | Fageraas et al. | |
| 2015/0304052 A1 | * | 10/2015 | Schemmann | H04B 10/572 398/68 |
| 2017/0268974 A1 | | 9/2017 | Brown et al. | |
| 2017/0269018 A1 | * | 9/2017 | Brown | G01F 23/24 |
| 2018/0227133 A1 | * | 8/2018 | Yang | H04L 12/10 |
| 2019/0229558 A1 | * | 7/2019 | Pigeon | A61N 1/3787 |

OTHER PUBLICATIONS

Grattan, K T V , "New developments in sensor technology—fibre and electro-optics", Measurement + Control, vol. 22, Issue 6, Jul. 1, 1989, pp. 165-175.

* cited by examiner

OPTICALLY POWERED SENSING SYSTEM AND METHOD FOR HAZARDOUS ENVIRONMENTS

CROSS-REFERENCE TO RELATED APPLICATIONS

The present application is a 35 U.S.C. § 371 national stage application of PCT Application No. PCT/AU2021/050263, filed on 24 Mar. 2021, which itself claims benefit of priority to Australian Provisional Patent Application Number 2020900899, filed 24 Mar. 2020, the contents of both of which are incorporated herein by reference.

FIELD OF THE INVENTION

The present invention relates to the field of fibre-optic sensing systems for reading a large number of sensors and, in particular, in preferred embodiments, discloses a process of utilising a single monomode fiber (a.k.a. single-mode fibre) for both data transmission and power delivery, requiring very low optical power.

The present disclosure claims benefit of priority to Australian Provisional Patent Application Number 2020900899, filed 24 Mar. 2020, the contents of which are incorporated herein by reference.

BACKGROUND OF THE INVENTION

Any discussion of the background art throughout the specification should in no way be considered as an admission that such art is widely known or forms part of common general knowledge in the field.

A sensing system typically consists of (i) an interrogation unit with convenient access to power and communication infrastructures, e.g. a remote terminal unit (RTU) or a programmable logic controller (PLC); (ii) a number of sensors in remote/hazardous/inaccessible locations; and (iii) a network that connects the sensors to the interrogation unit.

It is often desirable not to have any battery or mains power at the sensors' location, especially in hazardous environments or when access is difficult and maintenance costs are high. However, power is often required at the sensor location to perform three main functions: including measuring a change in the physical status of the sensor, conditioning the signal, and communicating with the interrogation unit.

There are many types of networks that can be used to connect sensors to an interrogation unit. These networks can be broadly subdivided into two categories: wired, such as copper wires or optical fibre, and wireless, such as WiFi or Zigbee. Wired systems are often preferred when reliability is crucial, especially when safety is involved. In some situations, wireless networks cannot be deployed because the transmission distance is too short, as it is the case for radio waves propagating under water. Among wired systems, optical fibre transmission is in general preferred over copper because of its ability to cover long distances, immunity to EMI, ease of multiplexing, safety, and bandwidth. There are many ways to transmit information over an optical fibre. The most common in industrial networks is using laser diode-based transceivers, sending and receiving light at both ends of the optical link between the sensor and the interrogation unit. When sensors are part of a network, which is the most common and desirable case, a communication protocol must be used to manage transmission of information from the sensor to the head-end interrogation unit. Most of the communication protocols used today (e.g. Ethernet/IP, WiFi, Foundation fieldbus) require two-way communication between the sensor and the head-end interrogation unit.

It would be desirable to have all the advantages of optical fibre sensing systems without requiring power at the sensor location.

One possibility is to use power-over-fibre to deliver power to the sensor optically, but there are several limitations at present with this approach: (i) intrinsic safety requirements in hazardous environments limit the maximum amount power that can be safely delivered optically. For example, 150 mW is the limit for intrinsic safety in mines, and this power limit is not enough to drive conventional sensors; (ii) in order to deliver high power (>300 mW) reliably, a multimode fibre must be used, which has limitations in terms of transmission distance and it is not the preferred choice to transmit information, thus requiring two separate optical networks for power delivery and data transmission; (iii) the cost of efficient power-over-fibre sources and converters is high.

SUMMARY OF THE INVENTION

It is an object of the invention, in its preferred form to provide for an Optically Powered Sensing System and Method for Hazardous Environments.

In accordance with a first aspect of the present invention there is provided a sensing system including: a sensor located in an external environment, the sensor including: an electrically powered sensor element sensing an environment variable and converting the sensing to a corresponding analogue electrical value measure; an electrically powered sensor value conversion system connected to the electrically powered sensor and converting the analogue electrical value measure to a corresponding digital measure, in addition to encoding the digital measure with sensor identification information, to produce sensed data information; a transducer element for sending the sensed data information over an optical input/output conduit; said Optical input/output conduit for inputting an optical electromagnetic power and outputting optical sensed data information; a coupler splitting a first portion of the optical power signal to an energy storage system; an energy storage system converting the first portion of the optical power signal into corresponding electrical energy and storing the electrical energy for on demand usage; with said electrically powered sensor element, said electrically powered sensor value conversion system being supplied with electrical power from said energy storage system.

Preferably, the sensing system also includes: an interrogation unit remotely attached to said optical input/output conduit, said interrogation unit including: an optical source for providing said optical power signal to said input/output conduit; an optical to electrical converter for converting received optical sensed data information into corresponding electrical data; and processing means for receiving the electrical form of said optical sensed data information and for decoding the information into corresponding sensed data information.

In some embodiments, the optical source is a broad band optical source. Preferably, the corresponding electrical data can be encoded utilising a one-directional asynchronous communication protocol. Preferably, the corresponding electrical data includes an identifier number for the sensor and a data value. The corresponding electrical data can be Manchester encoded for dispatch. The corresponding electrical data can include a preamble and a cyclic redundancy check. The data can be transmitted at regular periodic intervals. The optical input/output conduit can be a single mode fibre. In some embodiments, the coupler splits about 90% of the energy of said light to an energy storage system.

BRIEF DESCRIPTION OF THE DRAWINGS

Embodiments of the invention will now be described, by way of example only, with reference to the accompanying drawings in which.

DETAILED DESCRIPTION

The preferred embodiments of the present invention solve the problems of previous power-over-fibre approaches by: 1) transmitting information using passive optical transducers, which require extremely low power; 2) simplifying the sensor's electronics; and 3) introducing a new communication protocol that requires very low power at the sensor.

Suitable passive optical transducers can include those described or set out in PCT application number PCT/AU2013/000069 entitled "Optically Based Voltage Sensing Device and Method", the contents of which are hereby included by cross reference.

The preferred embodiments can be implemented by keeping the sensor in sleep mode most of the time and by moving most of the conditioning and additional functions from the sensor to the interrogation unit.

The preferred embodiment also provides for a one-directional (simplex) asynchronous communication protocol.

A sensing system incorporating one or more of the above ideas will allow using the same single-mode fiber for power and communication while keeping the optical power low enough to be intrinsically safe. In particular, sensors can be added to or removed from the network while operating respecting intrinsic safety requirements (hot swapping).

The advantages of some embodiments include: The ability to cover long distances (because of single-mode fibre properties), immunity to EMI (because the signal is optical), ease of multiplexing (in the optical domain), simplicity (plug and play sensors), intrinsic safety (because of low optical and electrical power), sensors can be made hot swappable, large bandwidth, intrinsic cyber security (sensors have no access to the higher level network), low cost (because low power), low maintenance (no battery, no software updates), and reliability (because wired).

Figure 1:
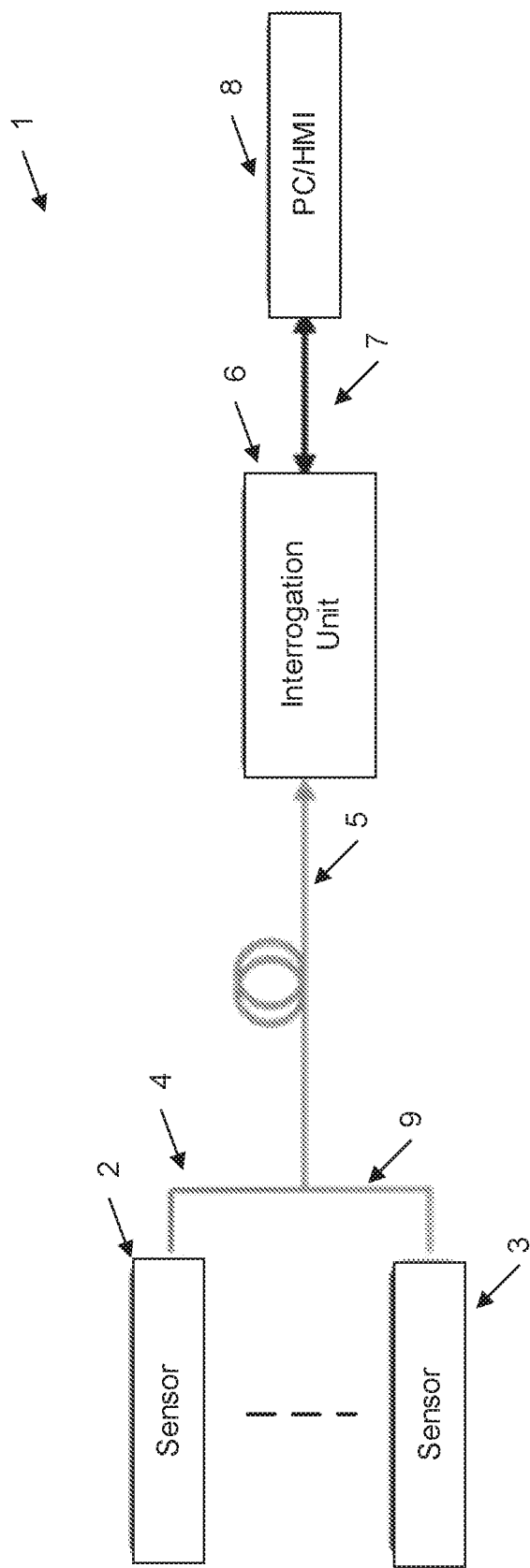
FIG. 1 illustrates schematically the environment of the sensing system, showing the sensors and the interrogation unit connected by a network.

Turning initially to FIG. 1, there is illustrated the operational environment of an embodiment 1 in that a series of sensors e.g. 2, 3 are interconnected to an interrogation unit 6 via optical fibers 4, 9, 5.

The interrogation unit can be powered and is responsible for communicating optically with each sensor and in turn is electrically interconnected to a computational type device 8 via electrical connection 7.

Figure 2:
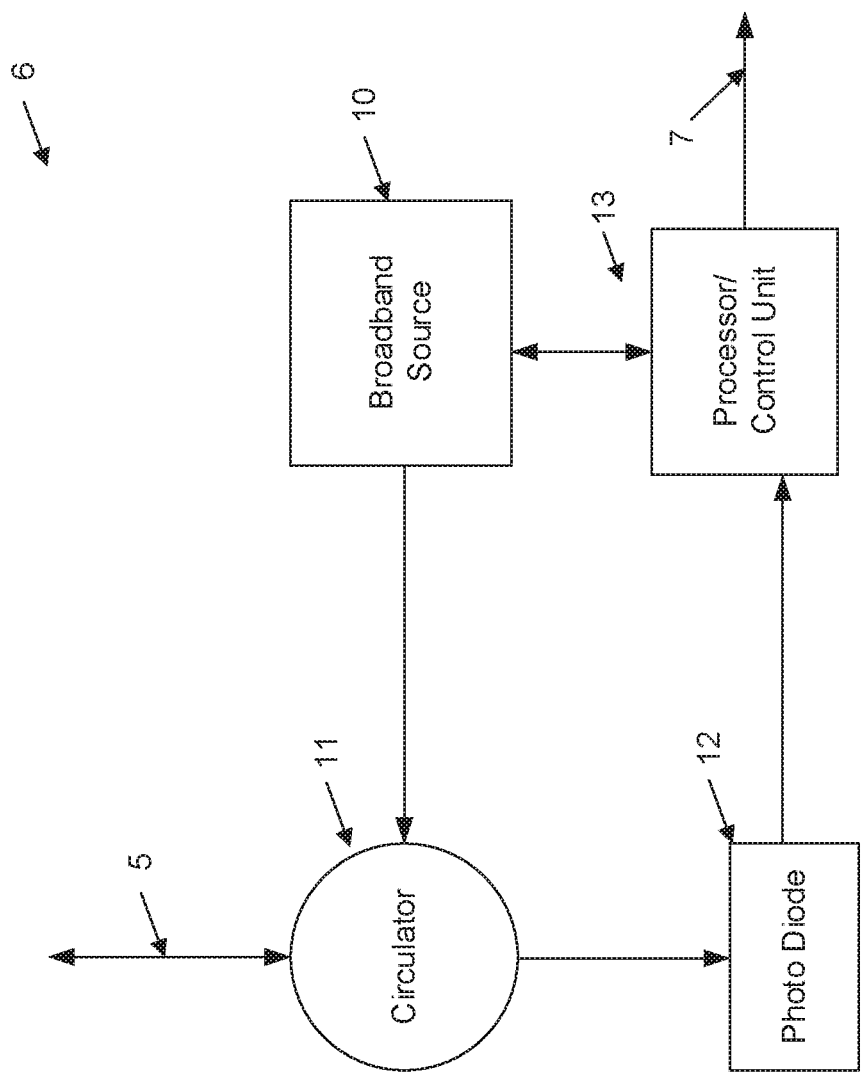
FIG. 2 illustrates schematically one form of interrogation unit.

Turning now to FIG. 2, there is illustrated one form of interrogation unit 6 in more detail. The interrogation unit 6 includes a broadband optical source 6, a circulator 11, a photodiode 12, a processor or control unit 13 and other electronic components.

In a first example embodiment, it will be assumed it is desired to measure temperature from a single Pt100 type sensor. Light generated by the source 10 is coupled into a single mode fiber 5 and delivered to the sensor.

Figure 3:
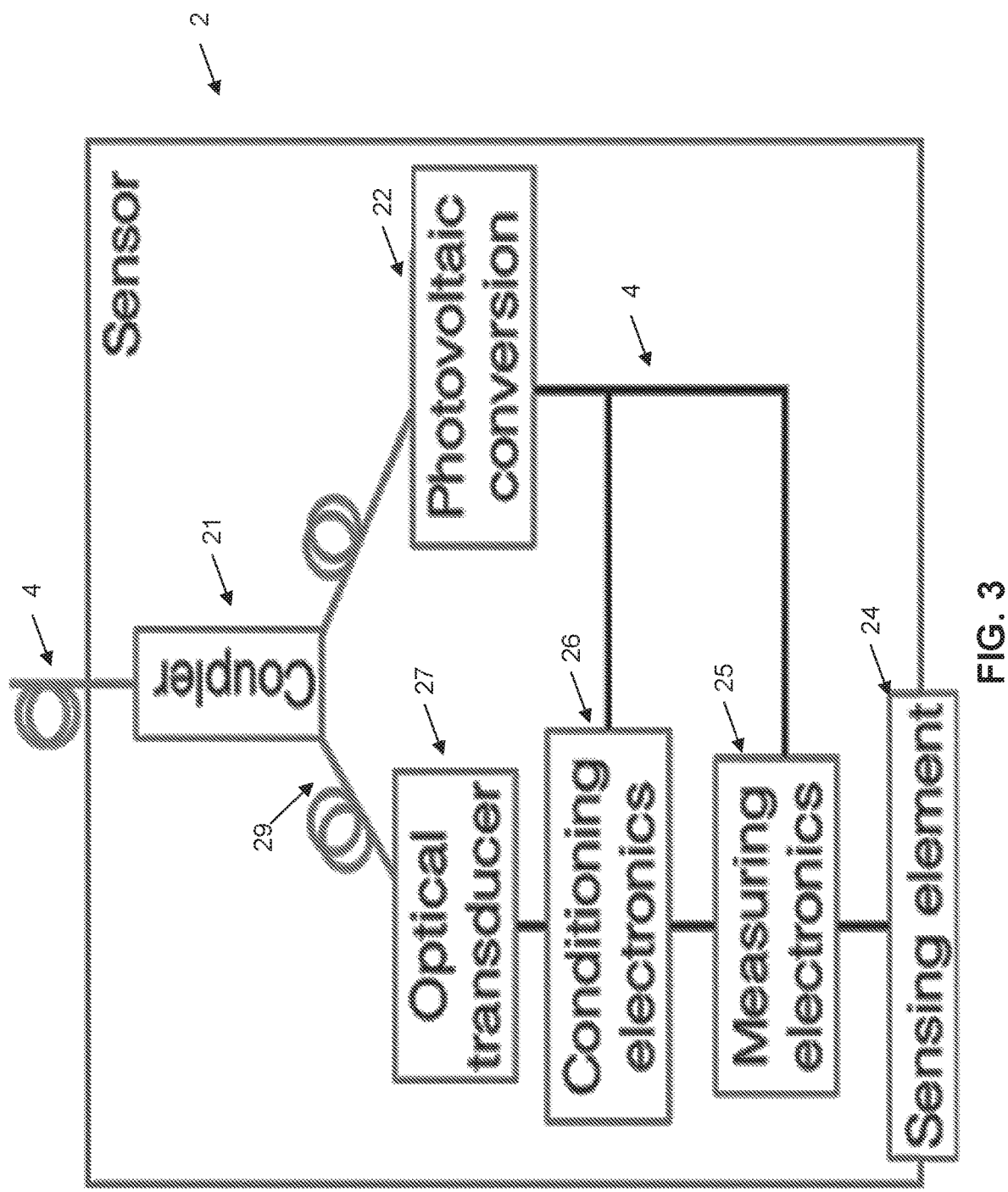
FIG. 3 illustrates one form of sensor.

FIG. 3 illustrates the sensor 3 of FIG. 1 in more detail. At the sensor, the incoming light 4 is split into an appropriate ratio, e.g. 10:90, by an optical coupler 21. The 90% output of the coupler goes to one inexpensive InGaAs photodiode 22, which generates a current and, through a specialised voltage booster with low startup voltage, generates a suitably high voltage, e.g. 5V, for charging a large capacitor, e.g. 2.2 mF. The capacitor is used to store energy and power the sensor's electronics with a suitable output voltage, e.g. 3.3V. The electronic components include a low power ADC and a microcontroller 25 that measure the Pt100 sensing element's 24 resistance and convert it into a digital number with the desired resolution. The digital number is transmitted at 32 kbs together with an identification code unique to the type of sensor. The total number of bits transmitted is 32. This information is Manchester encoded and sent during few milliseconds by applying the corresponding voltage to a passive optical transducer 27. This procedure is repeated at regular intervals. For every cycle the electronics is on for few milliseconds and in sleep mode for the rest of the time. This allows significantly reducing the average power consumption if the interval is larger than the ON time. Light emitted by the passive optical transducer 27 is carried over the same single mode optical fibre 29, 4, back to the interrogation unit.

Returning to FIG. 2, in the interrogation unit, reflected light intensity (proportional to the voltage applied to the passive optical transducer 27 of FIG. 3) is passed through circulator 11 and measured by the photodiode 12, and converted into an electrical signal. This electrical signal contains the 32 transmitted bits, that allow determining the sensor's identity and the transmitted value. This value is interpreted by the electronics of the Microcontroller 13 based on the sensor's identity. Calibration curves are stored in the interrogation unit are used to calculate the sensed temperature. The temperature value is then added to a buffer. Values in the buffer are read 7 at regular intervals and presented in output to the next layer of the monitoring system (a PC, a webpage, a SCADA, a PLC, etc.) through a suitable communication protocol, e.g. Ethernet/IP. The interrogation unit communicates with a PC (or similar) providing a human machine interface (HMI). The reading intervals can have the same duration as the measurement intervals in the sensor, so the sensing system can work in real-time with appropriate software/hardware installed in the interrogation unit. This protocol does not require synchronization. The beginning of a data sequence can be detected by a threshold crossing or by identifying a preamble sequence added to the transmitted data.

Other Embodiments

The arrangement described above can be extended to address multiple sensors over the same cable by using wavelength division multiplexing (a wavelength per sensor), spatial division multiplexing (a fiber core per sensor), mode division multiplexing (a mode per sensor), time division multiplexing or a combination of these approaches.

Other sensor devices can be used. For example, the sensor can be a pressure sensor, a gas sensor, a strain gauge sensor, a thermocouple, etc.

Two or more photodiodes connected in series or in parallel can be used at the sensor to convert optical power into electrical power more efficiently or more cost-effectively. In this case the optical coupler must have 3 or more output fibers with appropriate splitting ratios. A specialised photovoltaic power converter can be used with or without a voltage booster.

Local diagnostics at the sensor are possible. A technician can be provided access to the local electronics to check transmission. The optical source in the interrogation unit can be modulated to broadcast the status of each sensor from the interrogation unit to all sensors, e.g. by using Frequency Shift Keying. The technician can have access to the two pins of the photovoltaic photodiode (or of an additional photodiode) to measure this signal. This implementation would not require any extra power at the sensor.

The optical power delivered could be as low as 20 mW per sensor. The electronics on the sensor can consume less than 3 mW of electrical power.

In some embodiments, the capacitor can be replaced by (i) a pair of rechargeable batteries, one of which is trickle charged optically, while the other is used to supply power; (ii) a single rechargeable battery; (iii) a super-capacitor; (iv) nothing, just eliminated altogether.

In alternative embodiments, data can be encoded using any digital or analog protocol, as long as the power required at the sensor for generating and transmitting the data during each cycle is low.

The number of bit transmitted and the bit rate can be different to increase the bandwidth or to lower the power consumption. Additional information can be also transmitted to improve the performance, e.g. the local sensor temperature or the measurement from a second reference probe.

In some embodiments, the optical transducer can be replaced by a low threshold laser diode. The single-mode fiber can be replaced by a multi-mode fiber.

Further Embodiment

Figure 4:
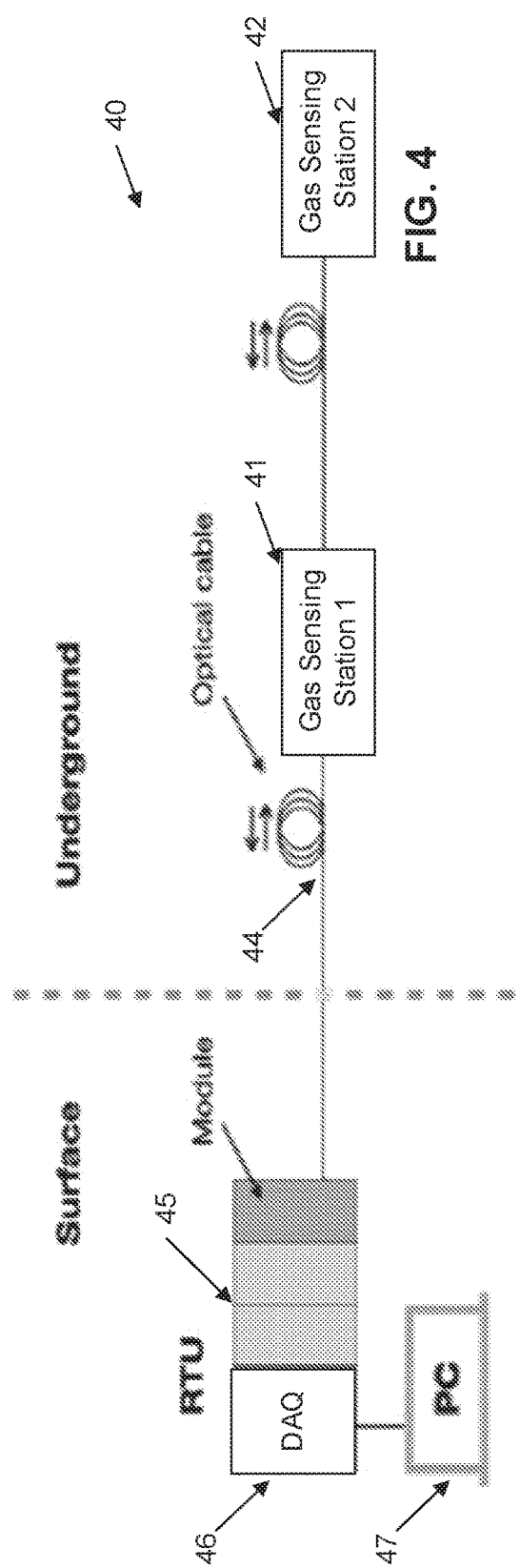
FIG. 4 illustrates schematically a further embodiment implementation for a coal mine.

A further embodiment will now be described with reference to FIG. 4 to FIG. 6.

This embodiment is particularly formed for sensing gas concentrations in an underground mine environment. Turning initially to FIG. 4, the embodiment 40 includes a series of gas sensing stations e.g. 41, 42, 'daisy chained' together via optical fibers e.g. 44 which is, in turn connected to a surface Remote Terminal Unit (RTU) 45. The RTU unit 45 includes a Data Acquisition (DAQ) unit, and is, in turn interconnected to a computer resource 47, for overall control and data recording.

Figure 5:
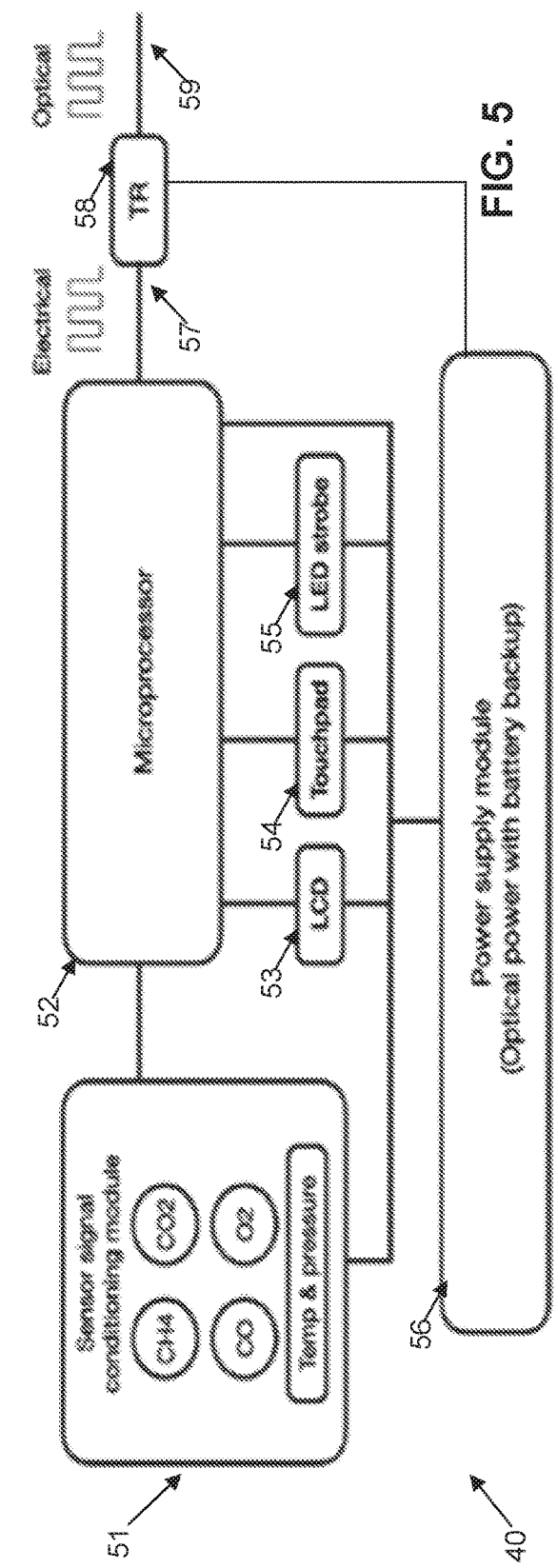
FIG. 5 illustrates schematically the form of a gas sensor station of FIG. 4.

Turning now to FIG. 5, there is shown schematically one form of arrangement of the gas sensor station 40. This station can include a series of low power sensors in a sensing signal conditioning module 51 for sensing the environment. The sensor signal conditioning module incorporates four gas sensor cells and a single sensor for temperature and pressure. The sensors are designed to consume ultra-low power while maximising the sensors performance.

The conditioned sensing signals are then processed by a microprocessor 52 which orchestrates all other info from LCD display 53, touchpad 54, LED strobe 55 etc, in addition to power supply level signals from power supply module 56. These are transformed into corresponding Manchester encoded digital signals for transmission. The electrical output is then output for conversion 58 to corresponding optical form for output transmission 59. Broad band optical input 59 is also converted to corresponding electrical signal for forwarding to power supply module 56 for charging the power supply module.

Figure 6:
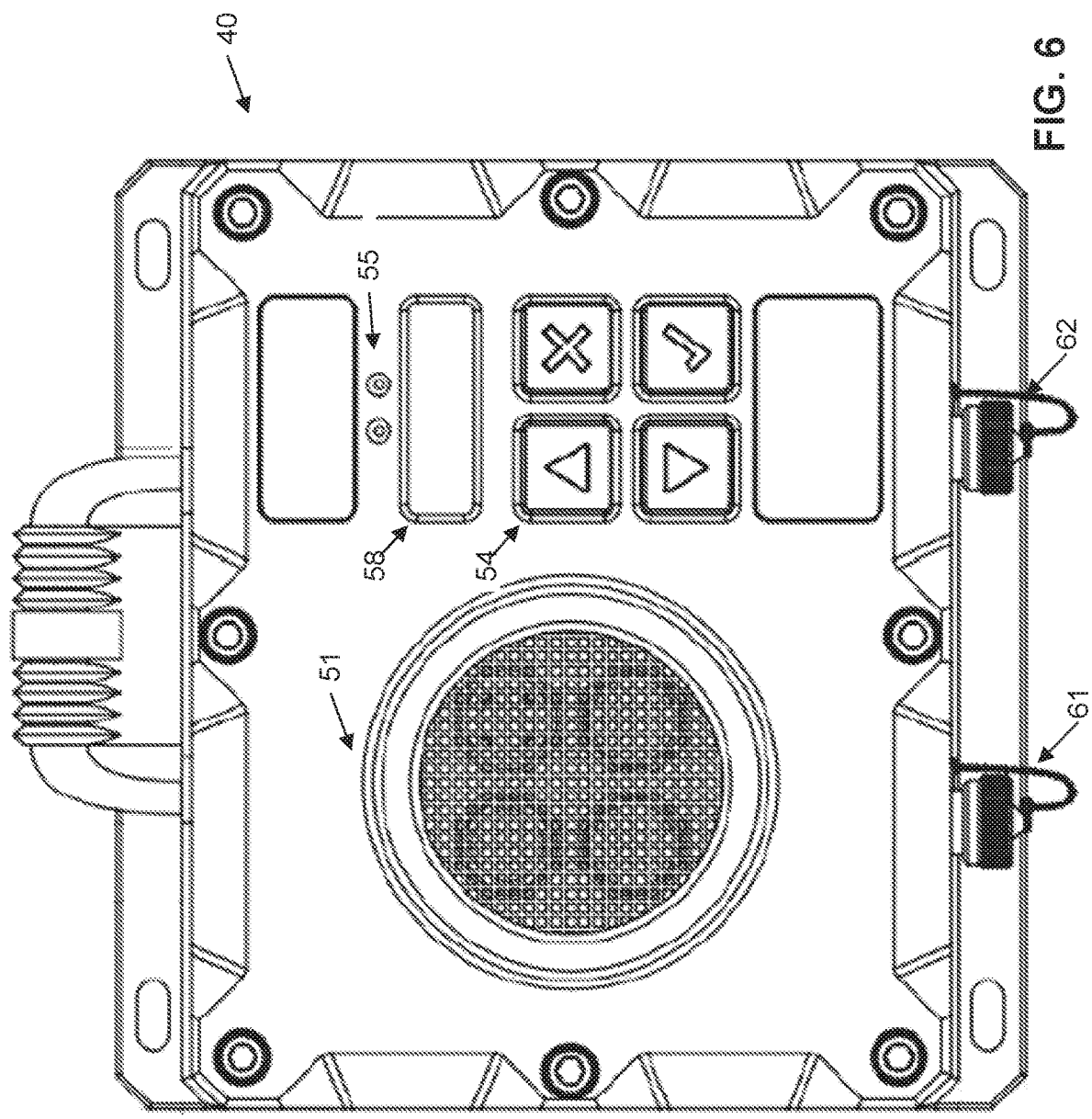
FIG. 6 illustrates a front plan view of one form of gas sensor station.

Turning to FIG. 6, there is illustrated one form of packaged gas sensor station 40. The sensor station includes sensor signal conditioning module 51, LCD 53, LED strobe 55 for indicating operational status and keypad 54. Optical fiber interconnects, 61, 62 are also provided.

Although this further embodiment was focused on gas monitoring, it is by no means limited to this specific application. The embodiments enable a new monitoring approaches especially under conditions where intrinsically safe monitoring over large areas (or long distances) are required. This includes petrochemical plants, ocean monitoring, geoseismic exploration and pipeline leak detection, including water, gas or oil. The embodiment have application to almost any type of sensing environment.

The embodiments also allow for the elimination of current loops for the transmission of signals, as the signal is transmitted optically. This allows for a significant simplification of the embodiment. In that the sensing element can have minimal complexity, allowing for significantly reduced power consumption.

Based on the technologies of power-over-fibre and optical transducers, there is provided an intrinsically safe, optically powered gas monitoring system supporting a number of gas monitoring stations and the one remote terminal unit (RTU) (45 of FIG. 4) connected via ruggedised optical cables for underground coal mine's real time gas monitoring.

Digital Optical Signal Transmission

When light comes in from the 'Light in' port 61 of gas sensor station about 5% of the light is diverted to an optical transducer, a passive device which converts an electrical signal to an optical signal as explained previously. The electrical signal the transducer receives inside the gas sensor uses Manchester encoded signal from the microprocessor. For each gas sensor, an identifier (ID), sensor readings, operation modes, levels of optical power and battery, etc, are encoded and transmitted in 8 Manchester packets. This digital electrical signal is then translated into optical signal by the transducer 58 and transmitted via the optical fibre back to the RTU to be decoded.

The light source is used both for powering and for signal transmission. To power the gas sensor, about at least 110 mW of optical power is used; and for signal transmission, a broad-band light with low noise at relatively low frequency is used. In addition, a protection circuit for overpower protection is required for intrinsic safety.

Turning back to FIG. 4, a DAQ module 46 is designed to decode and process the signal from the gas module. It is also powered by 12 V DC and draws around 200 mA current. It supports an Ethernet interface and data logging. The information of each sensor in the form of the 8 Manchester packets are read and logged to volatile SDRAM memory every second and given a timestamp. The realtime data of each sensor includes: Gas concentrations of $CH_4$, CO, $CO_2$ and $O_2$, Ambient temperature, Ambient barometric pressure, Operation modes, Optical power level, Battery level.

Interpretation

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A sensing system including:
a sensor located in an external environment, the sensor including:
an electrically powered sensor element sensing an environment variable and converting the sensing to a corresponding analog electrical value measure;
an electrically powered sensor value conversion system connected to the electrically powered sensor and converting the analog electrical value measure to a corresponding digital measure, in addition to encoding the digital measure with sensor identification information, to produce sensed data information;
a transducer element for sending the sensed data information over an optical input/output conduit;
said optical input/output conduit for inputting an optical power signal and outputting optical sensed data information;
a coupler splitting a first portion of the optical power signal to an energy storage system; and
an energy storage system converting the first portion of the optical power signal into corresponding electrical energy and storing the electrical energy for on demand usage;
with said electrically powered sensor element, said electrically powered sensor value conversion system being supplied with electrical power from said energy storage system, and
wherein said corresponding electrical data is encoded and sent utilising a one-directional asynchronous communication protocol, and
wherein said sensor periodically enters a low power sleep state followed by a higher power active state where information is transmitted by the sensor.

2. A sensing system as claimed in claim 1 further including:
an interrogation unit remotely attached to said optical input/output conduit, said interrogation unit including:
an optical source for providing said optical power signal to said input/output conduit;
an optical to electrical converter for converting received optical sensed data information into corresponding electrical data; and
processing means for receiving the electrical form of said optical sensed data information and for decoding the information into corresponding sensed data information.

3. A sensing system as claimed in claim 2 wherein said optical source is a broad band optical source.

4. A sensing system as claimed in claim 1 wherein said corresponding electrical data includes an identifier number for the sensor and a data value.

5. A sensing system as claimed in claim 1 wherein said corresponding electrical data is Manchester encoded for dispatch.

6. A sensing system as claimed in claim 1 wherein data is transmitted at regular periodic intervals.

7. A sensing system as claimed in claim 1 wherein said optical input/output conduit includes a single mode fiber.

8. A sensing system as claimed in claim 1 wherein said coupler splits about 90% of the energy of said light to an energy storage system.

9. A sensing system as claimed in claim 1 wherein said energy storage system includes a plurality of conversion units for converting the first portion of the optical power signal into corresponding electrical energy.

10. A sensing system as claimed in claim 1 wherein the optical power signal is less than 150 mW.

11. A sensing system as claimed in claim 1 wherein the electrically powered sensor element comprises an optically based voltage sensing device.

* * * * *